US010537298B2

(12) United States Patent
Martino et al.

(10) Patent No.: US 10,537,298 B2
(45) Date of Patent: Jan. 21, 2020

(54) METHOD AND DEVICE TO ADJUST A CEPHALOMETRIC EXTRA ORAL DENTAL IMAGING DEVICES

(71) Applicant: TROPHY, Croissy Beaubourg (FR)

(72) Inventors: Olivier Martino, Marne la Vallee (FR); Yann Lecuyer, Paris (FR)

(73) Assignee: TROPHY, Croissy Beaubourg (FR)

( * ) Notice: Subject to any disclaimer, the term of this patent is extended or adjusted under 35 U.S.C. 154(b) by 238 days.

(21) Appl. No.: 15/520,474

(22) PCT Filed: Dec. 4, 2014

(86) PCT No.: PCT/IB2014/002969
§ 371 (c)(1),
(2) Date: Apr. 20, 2017

(87) PCT Pub. No.: WO2016/087893
PCT Pub. Date: Jun. 9, 2016

(65) Prior Publication Data
US 2017/0311915 A1    Nov. 2, 2017

(51) Int. Cl.
*A61B 6/00* (2006.01)
*A61B 6/04* (2006.01)
(Continued)

(52) U.S. Cl.
CPC .............. *A61B 6/505* (2013.01); *A61B 6/14* (2013.01); *A61B 6/501* (2013.01); *A61B 6/588* (2013.01); *A61B 6/589* (2013.01); *G06T 7/33* (2017.01)

(58) Field of Classification Search
CPC .... A61B 6/04; A61B 6/08; A61B 6/14; A61B 6/501; A61B 6/505; A61B 6/587; A61B 6/588; A61B 6/589; G06T 7/33
See application file for complete search history.

(56) References Cited

U.S. PATENT DOCUMENTS 3,536,913 A * 10/1970 Huchel .................... A61B 6/14
                                                    378/168
3,790,803 A *  2/1974 Phillips ................... A61B 6/14
                                                    378/170
(Continued)

FOREIGN PATENT DOCUMENTS

JP        2004/229787        8/2004

OTHER PUBLICATIONS

International Search Report for International application No. PCT/IB2014/002969, dated Jul. 16, 2015, 2 pages.
(Continued)

*Primary Examiner* — Mark R Gaworecki (57) ABSTRACT

An extra-oral imaging apparatus is intended to obtain a cephalometric image of a portion of a head of a patient. Exemplary apparatus embodiments of cephalometric functionality of such extra-oral imaging apparatus can include a cephalometric support mounted to a base of the imaging system that is configured to position a cephalometric sensor about a cephalometric imaging area so that x-rays impinge the cephalometric sensor after radiating the cephalometric imaging area. A cephalometric patient positioning unit mounted to the cephalometric support can be positioned between an x-ray source of the x-rays and the cephalometric sensor. A cephalometric alignment sight can be mounted to patient positioning unit to provide a visual indication of alignment between the x-ray source and the mounted alignment sight/cephalometric sensors. Exemplary methods are provided that can use such exemplary cephalometric alignment sights and/or install cephalometric functionality to imaging systems using the same.

20 Claims, 9 Drawing Sheets

(51) Int. Cl.
*G06T 7/33* (2017.01)
*A61B 6/14* (2006.01)

(56) References Cited

U.S. PATENT DOCUMENTS

| | | |
|---|---|---|
| 4,088,893 A | 5/1978 | Schroeder |
| 4,683,582 A | 7/1987 | Spolyar |
| 2007/0297564 A1 | 12/2007 | Rotondo et al. |

OTHER PUBLICATIONS

Written Opinion dated Jun. 6, 2017; 6 pages.
EPO Communication dated Jan. 19, 2019; 2 pages.

* cited by examiner

METHOD AND DEVICE TO ADJUST A CEPHALOMETRIC EXTRA ORAL DENTAL IMAGING DEVICES

CROSS REFERENCE TO RELATED APPLICATIONS

This application claims the benefit of and is a U.S. National Phase filing of PCT Application PCT/IB14/02969 filed Dec. 4, 2014, entitled "METHOD AND DEVICE TO ADJUST A CEPHALOMETRIC EXTRA ORAL DENTAL IMAGING DEVICES", in the name of Martino et al., which is incorporated herein in its entirety.

FIELD OF THE INVENTION

The invention relates generally to the field of dental x-ray imaging, and more particularly, to a cephalometric x-ray imaging functionality for dental applications. Further, the invention relates to a cephalometric dental imaging apparatus and/or methods.

BACKGROUND

Cephalometric imaging (or transillumination imaging) is regularly used by dental practitioners, for example, in orthodontic applications. For cephalometric imaging techniques, an image of the x-ray radiated skull of the patient is projected on an x-ray sensitive surface located away from the x-ray source using a cephalometric arm. In most of the cases, the sensor is positioned at the extremity of a long cephalometric arm and is positioned at a distance about 1.7 meters away from the x-ray source. The necessity to have the sensor positioned far away from the x-ray source originates from the necessity to have an approximately equal magnitude factor for every part of the patient's skull. The imaging process may consist in one single shot of the patient's skull with the x-ray beam impinging a full (e.g., square) sensor after radiating the patient. As an alternative to decrease the size of the sensor, a linear elongated sensor can be used in association with a linearly elongated (e.g., vertical) slit-shaped collimator that aims at shaping the x-ray beam before the x-ray beam radiates the patient. The patient is positioned between the elongated collimator and the elongated sensor. A linear scan can be performed by horizontally translating a vertically elongated sensor and a vertically elongated collimator and changing the direction of the x-ray beam accordingly through the use of a primary collimator positioned in front of the X-ray source. The images collected during the scan are merged together to form a projection of the patient's skull. In the cephalometric or skull imaging technique, the patient can be positioned facing the x-ray beam or in a profile position.

In order to obtain a skull profile image of the best quality, the sagittal plane of the skull must be parallel to the plane of the sensor at the time of the imaging and orthogonal to the median line of the x-ray beam. Consequently, when a cephalometric imaging apparatus is first installed in a dental site by a technician, it is necessary to adjust the position of the whole cephalometric imaging module, comprising the x-ray sensor and a patient holder, relative to the x-ray source, prior to any cephalometric imaging of patients. According to the prior art, at least two radiopaque markers are located on the patient holder and a first x-ray control image of the patient holder (without any patient) is carried out. If the images of the at least two markers superimpose on the x-ray image, the cephalometric module is conveniently or correctly positioned relative to the x-ray source. On the contrary, if the images of the two markers do not superimpose, the cephalometric module is misaligned relative to the x-ray source and needs to be repositioned before capturing a second control image or additional control images.

One drawback of the prior art process is because the technician who installs the cephalometric imaging device does not know, at the time he changes the adjustment of the cephalometric module, whether the new adjustment is correct. Only subsequent control images taken after adjustment will give an assessment of the quality of the adjustment. Accordingly, the cephalometric installation requires an adjustment process including a repeated, back and forth method of (i) successive adjustments of the cephalometric module to the x-ray source and (ii) successive assessments by taking a follow-up control image. This repetitious installation process is highly cumbersome, time consuming, and/or increases the cost of the installation of the cephalometric imaging device by the technician.

It can be appreciated that there is still a need for installation apparatus and/or methods that can provide a cheaper, rapid, accurate and/or real time assessment of a correctness of an installation/adjustment of a cephalometric module and/or dental cephalometric imaging device.

SUMMARY

An aspect of this application is to advance the art of medical digital radiography, particularly for dental cephalometric applications.

Another aspect of this application is to address, in whole or in part, at least the foregoing and other deficiencies in the related art.

It is another aspect of this application to provide, in whole or in part, at least the advantages described herein.

An advantage offered by apparatus and/or method embodiments of the application relates to providing a visual indication of alignment between an x-ray source and cephalometric imaging sensor.

Another advantage offered by apparatus and/or method embodiments of the application relates to providing a real-time indication of alignment between an x-ray source and cephalometric imaging sensor.

Another advantage offered by apparatus and/or method embodiments of the application relates to an extra-oral dental radiographic imaging system including a cephalometric support configured to position a cephalometric imaging sensor so that x-rays impinge the cephalometric sensor after radiating a cephalometric imaging area, because an x-ray source includes a target and the cephalometric support or the cephalometric imaging sensor includes an alignment sight attachable to point toward the target.

According to one aspect of the disclosure, there is provided a method for servicing a cephalometric imaging unit to an extra-oral imaging system that can include mounting a cephalometric imaging unit to a system base, the system base adjustable in at least one direction and configured to support an x-ray source, the cephalometric imaging unit configured to mount a cephalometric sensor, the cephalometric imaging unit including a cephalometric patient positioning unit positioned between the x-ray source and the cephalometric sensor so that x-rays impinge the cephalometric sensor after radiating the cephalometric patient positioning unit; mounting a cephalometric alignment device to the cephalometric patient positioning unit; and aligning the cephalometric imaging unit in real-time using a visual indication of alignment to the x-ray source provided by the cephalometric alignment device.

According to one aspect of the disclosure, there is provided extra-oral imaging system that can include a base adjustable in at least one dimension; a cephalometric support mounted to the base and configured to position a cephalometric sensor about a cephalometric imaging area so that x-rays impinge the cephalometric sensor after radiating the cephalometric imaging area; a cephalometric patient positioning unit mounted to the cephalometric support, the cephalometric patient positioning unit positioned between an x-ray source and the cephalometric sensor, the cephalometric patient positioning unit including at least one patient support having a controllable position relative to the cephalometric sensor or the x-ray source; and an alignment sight at least temporarily mounted to the at least one patient support to provide a visual indication of alignment between the x-ray source and the mounted alignment sight.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other. Some exaggeration may be necessary in order to emphasize basic structural relationships or principles of operation. Some conventional components that would be needed for implementation of the described embodiments, such as support components used for providing power, for packaging, and for mounting and protecting x-ray system components, for example, are not shown in the drawings in order to simplify description.

DESCRIPTION OF EXEMPLARY EMBODIMENTS

The following is a description of exemplary embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal. The term "actuable" has its conventional meaning, relating to a device or component that is capable of effecting an action in response to a stimulus, such as in response to an electrical signal, for example.

Apparatus and/or method embodiments according to the application aim at facilitating an installation process by giving the technician a highly precise real time assessment of the correctness of the adjustment of the cephalometric module.

Figure 1A:
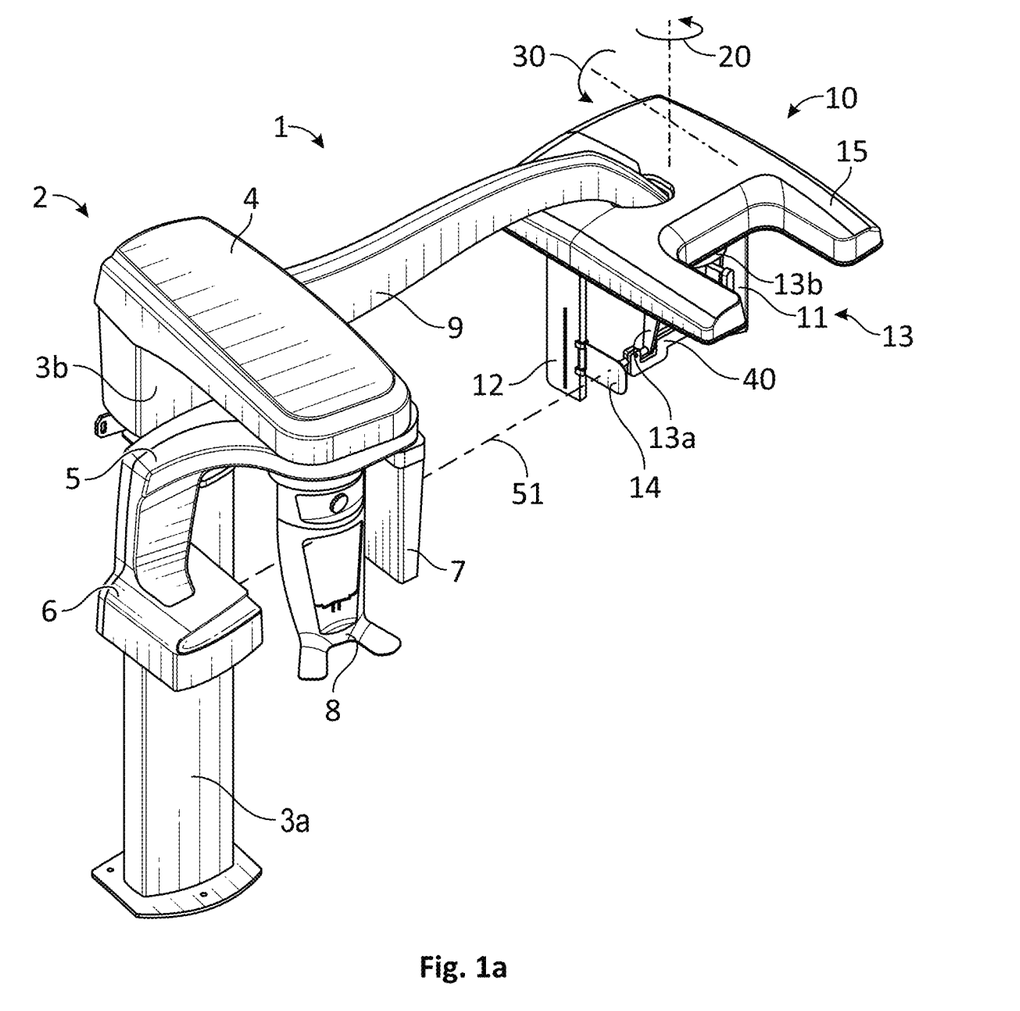
FIGS. 1a-1b are diagrams that show a perspective view and side view of an extra-oral dental imaging system including a cephalometric imaging unit with an attached alignment device according to a first exemplary embodiment of the application.
Figure 1B:
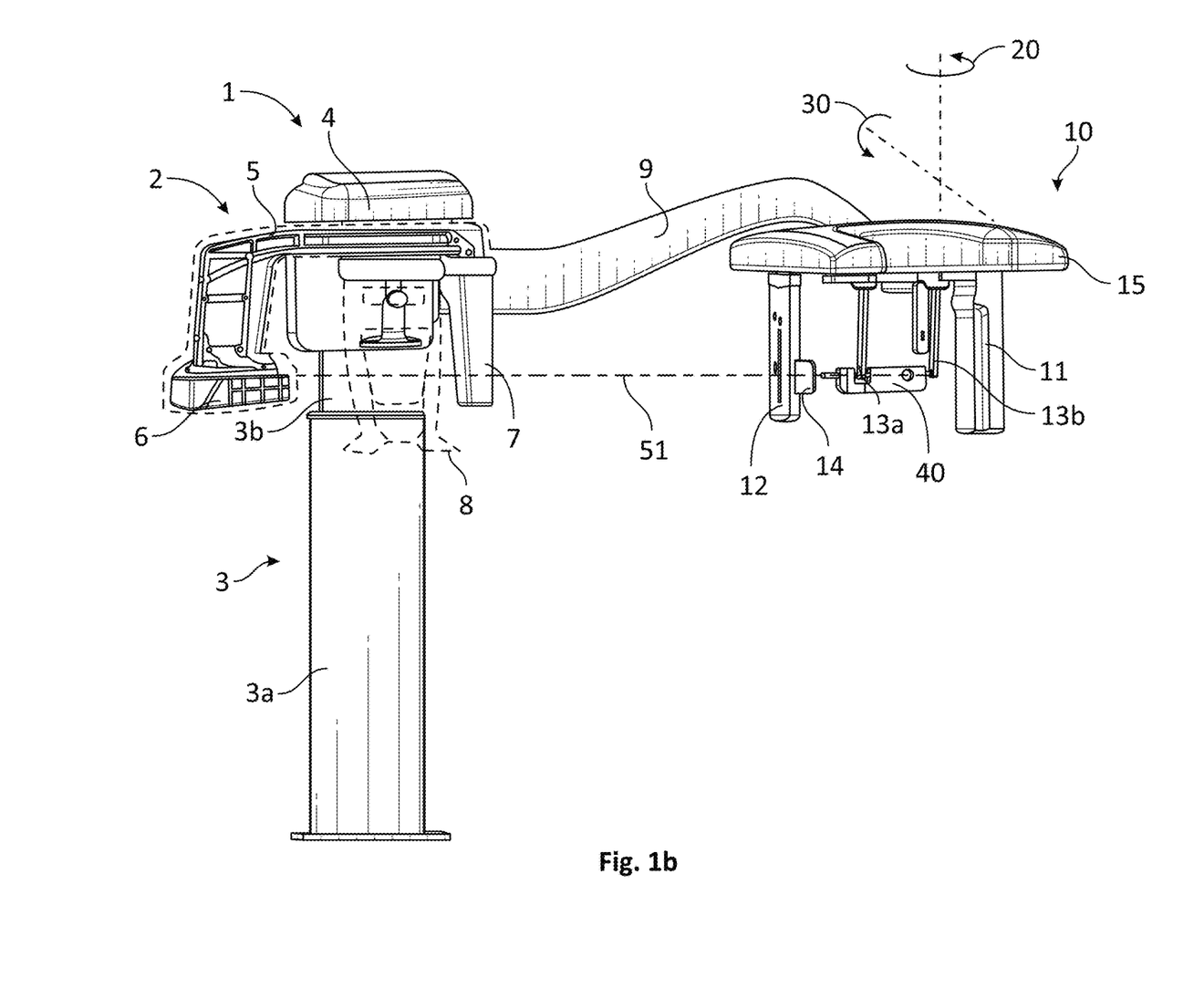

FIGS. 1a-1b are diagrams that shows an exemplary extra-oral dental imaging system that includes a multimodal cephalometric x-ray imaging device 1. As shown in FIG. 1a, the multimodal cephalometric x-ray imaging device 1 includes a panoramic and/or Computerized Tomography (CT) imaging device 2 to which a cephalometric imaging module 10 is added at the end of a cephalometric arm 9. The panoramic and/or CT imaging device 2 can include a support structure that can include a support column. The support column may be adjustable. For example, the support column may be telescopic vertical column 3 and may include an upper part 3b sliding inside a lower part 3a. A horizontal mount 4 is supported or held by the vertical column 3 and can support a rotatable gantry 5. An x-ray source 6 and a first x-ray imaging sensor 7 are attached or coupled to the gantry 5 in correspondence (e.g., opposite, aligned) to each other. The first x-ray sensor 7 may include one or both of a panoramic (e.g., slit-shaped) sensor or a Computerized Tomography (e.g., rectangular, square-shaped) sensor. A first patient positioning and holding system 8 can be positioned between the x-ray source 6 and the first x-ray imaging sensor 7 so that the x-ray beam originating from the x-ray source 6 impinges the sensor 7 after radiating a first imaging area or the patient in the first imaging area. The first patient positioning and holding system 8 can include a shield that can include a forehead support and two handles at its base. The patient can then grasp the handles of the first patient positioning and holding system 8 and remain motionless during the CT scan or panoramic scan. The first patient positioning and holding system 8 can optionally include a chin rest, a bite stick, other head supports and/or other alignments aids including markers, slits, positioning devices, guides, or projected lights. A cephalometric device (9, 10) alone, that is to say without the panoramic and/or CT device (e.g., without sensor 7 and first patient positioning and holding system 8) can also be contemplated. In that case, the vertical column 3, and the attachment of the cephalometric arm 9 to the column 3 can follow exemplary embodiments described herein for alignment with an x-ray source (e.g., x-ray source 6) coupled to the column 9.

The cephalometric imaging module 10 can include a cephalometric plate 15 supporting a cephalometric sensor 11, a collimator 12 and a patient holder or second patient positioning and holding system 13. When switching from a panoramic or CT imaging mode to the cephalometric imaging mode, the panoramic or CT sensor 7 is retracted so that the x-ray source 6 faces the cephalometric sensor 11 and the x-ray beam from the x-ray source 6 can strike the cephalometric sensor 11. The second patient positioning and holding system 13 can include two ear rod holders 13a and 13b supporting the ear rods 13d and 13e and a nasion 13c (see FIG. 3) to hold and position the patient's head. The cephalometric sensor 11 and the second patient positioning and holding system 13 can be coupled to or linked to the cephalometric plate 15 in such a way that a straight line linking both ear rods 13d and 13e (e.g., through a center of each ear rod) intercepts the cephalometric sensor 11 orthogonally. Optionally, a Frankfurt plane indicator 14 materializes the Frankfurt plane of the patient in order to tilt conveniently (e.g., position correctly for imaging) the patient's head. The Frankfurt plane of the patient is the plane containing the ear canals and the bottom points of the eye sockets. In one embodiment, the horizontal mount 4 supporting the gantry 5 and the x-ray source 6 and the cephalometric arm 9 supporting the cephalometric imaging module 10 and the cephalometric sensor 11 can both be attached to the telescopic column 3b. Consequently, cephalometric imaging system such as shown in FIG. 1a can be positioned at any height depending on the patient's size while the x-ray source 6 and the cephalometric sensor 11 remain at the same vertical position.

Figures 2A, 2B, 2C:
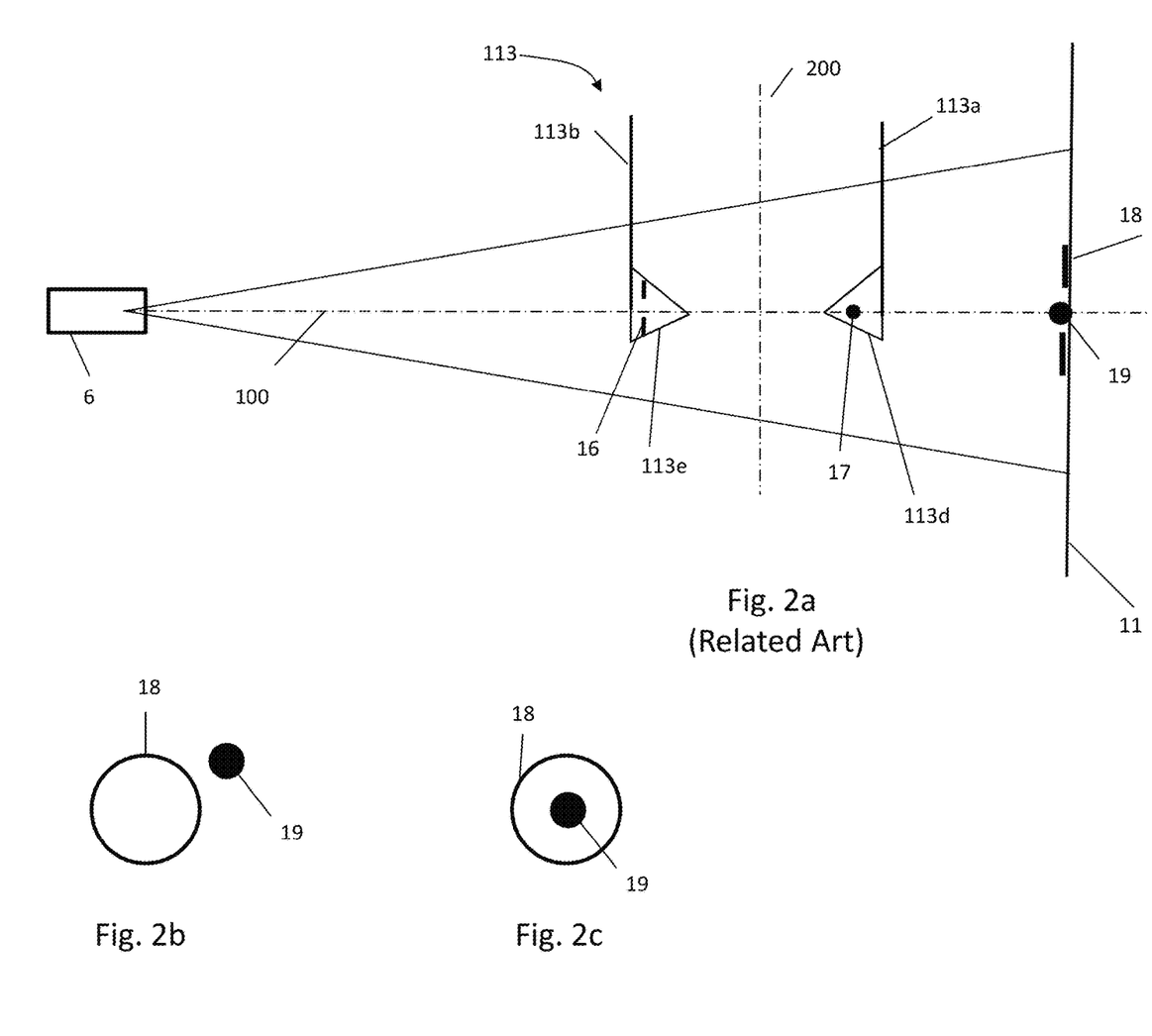
FIG. 2a is a diagram that shows a related art cephalometric patient holder with two radiopaque markers incorporated therein, positioned relative to a center line of an x-ray beam and a sagittal plane of a patient.
FIG. 2b is a diagram that shows an x-ray image of two radiopaque markers incorporated in the cephalometric patient holder of FIG. 2a in the case of a misalignment of a cephalometric module and an x-ray source.
FIG. 2c is a diagram that shows an x-ray image of two radiopaque markers incorporated in the cephalometric patient holder of FIG. 2a in the case of a correct alignment of a cephalometric module and an x-ray source.

FIG. 2a is a diagram that shows a related art cephalometric patient holder with two radiopaque markers incorporated therein, positioned relative to a center line of an x-ray beam and a sagittal plane of a patient. As shown in FIG. 2a, a radiopaque ring 16 is incorporated on one ear rod 113e near the extremity of one ear rod holder 113b and a radiopaque ball 17 is incorporated on a paired ear rod 113d near the extremity of a paired ear rod holder 113a of a patient holder 113. The axis passing through the two ear rods 113d, 113e is orthogonal to the x-ray sensor 11 and aligned to a center line 100 of an x-ray beam of the x-ray source 6. Consequently, the sagittal plane 200 of a patient positioned on the holder 113 is parallel to the sensor 11. In the method of cephalometric module alignment according to the related art device shown in FIG. 2a, an x-ray exposure of the cephalometric patient holder 113 is carried out and the image of the radiopaque ring 16 and radiopaque ball 17 markers captured by the cephalometric sensor 11 is clearly visible. When a point-like image 19 of the radiopaque ball 17 is outside of a circle-like image 18 of the radiopaque ring 16 (e.g., as shown in FIG. 2b), the center line 100 of the x-ray beam does not coincide with the axis passing through the ear rods 113d and 13e and then the patient holder 113 is misaligned with the x-ray source 6. As the patient holder 113 is in a rigid and fixed relationship with the cephalometric module 10, the technician must then reposition the whole module 10 relative to the cephalometric arm 9 before carrying out another alignment evaluation using another x-ray exposure and image review of the cephalometric patient's holder 113 (e.g., radiopaque ball and ring 16, 17). This re-positioning can include in rotating the cephalometric module 10 about at least one of the two respective axis 20 and 30 (see FIGS. 1a-1b). After re-positioning, another image of the holder 113 must be captured. If the point-like image 19 of the ball 17 is inside the circle-like image 18 of the ring 16 in the re-positioned image (as shown in FIG. 2c), the patient holder 113 is correctly aligned with the x-ray source 6 and the adjustment of the cephalometric module 10 is completed. Further, the center line 100 of the x-ray beam is aligned with the two ear rods 113d, 113e. As shown in FIG. 2a, the alignment of the center line 100 of the x-ray beam with the two ear rods 113d, 113e makes sure that the x-ray beam will be aligned with the two ear canals of the patient positioned in the patient's holder 113 whenever subsequently imaged. Further, the alignment ensures the sagittal plane of the patient will be orthogonal to the median line 100 of the x-ray beam.

Figure 3:
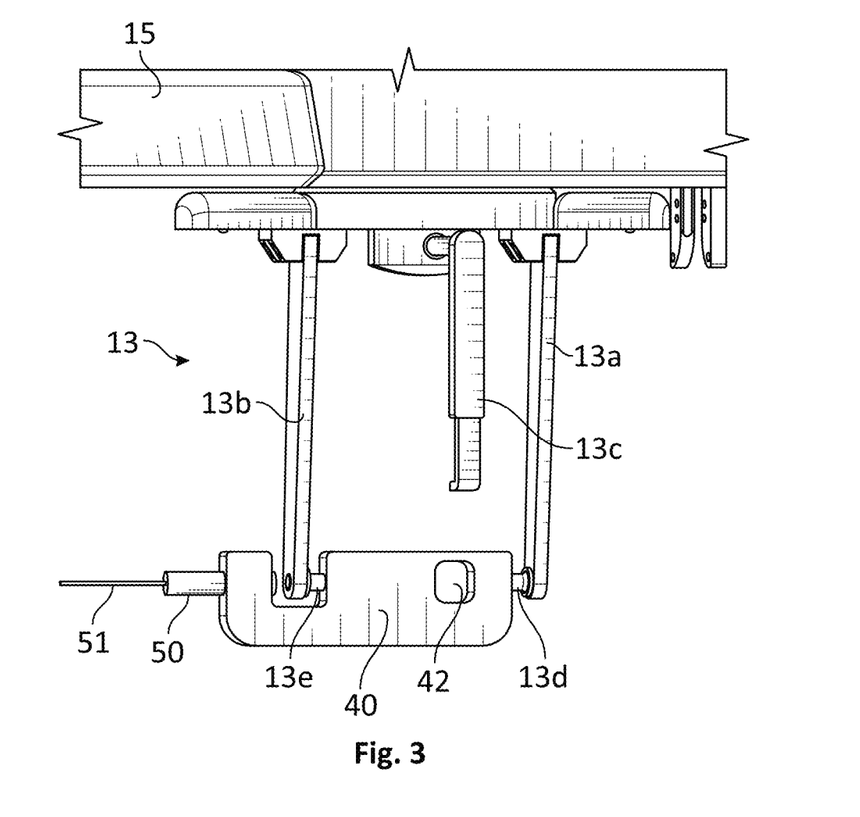
FIG. 3 is a diagram that shows an exemplary sight embodiment mounted on a support holder to assess the correctness of a cephalometric module installation/adjustment relative to a system x-ray source according to the application.

FIG. 3 is a diagram that shows an exemplary sight embodiment mounted on a support holder to assess alignment or correctness of a cephalometric module installation/adjustment relative to a system x-ray source according to the application. As shown in FIG. 3, a sight 40 can be positioned between and held by the two ear rods 13d and 13e of the second patient positioning and holding system 13. In one embodiment, a laser 50 is inserted in a bore 43 of the sight 40. The laser 50 emits a laser beam 51 towards the x-ray source 6.

Figure 4:
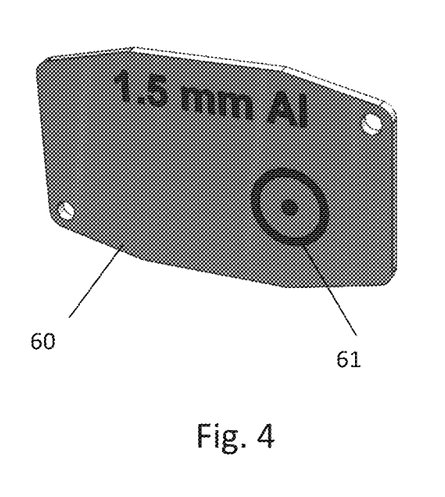
FIG. 4 is a diagram that shows an x-ray filter embodiment including a target according to the application.

FIG. 4 is a diagram that shows an x-ray filter embodiment including a target according to the application. As shown in FIG. 4, an x-ray filter 60 can be screwed on the metallic cartridge of the x-ray source 6. The x-ray filter 60 can be made of any conventional filter materials, but is preferably made of aluminum. The role of the filter 60 will now be described. The x-ray beam emitted by the x-ray source 6 is polychromatic. The drawback of a large wave length of the spectra of the polychromatic x-ray beam is that the less energetic radiation creates large metallic artifacts when the imaged patient skull or dental arch contains metal (e.g., metallic crowns). The filter 60 is intended to absorb the less energetic radiations of the spectra. By filtering the less energetic radiation, it is possible to diminish the importance of the metallic artifact in x-ray images caused by the presence of metallic objects (e.g., crowns) inside the patient's head and can significantly increase the image quality in that case. Embodiments of the filter 60 according to the application provide a target 61 for use during alignment (e.g., using a generated directional beam) by the sight 40. The target 61 can include any known aimable configuration such as a bulls eye, cross-hatch, "X", concentric markings or at least one point and/or circle as shown in FIG. 4.

Figure 5:
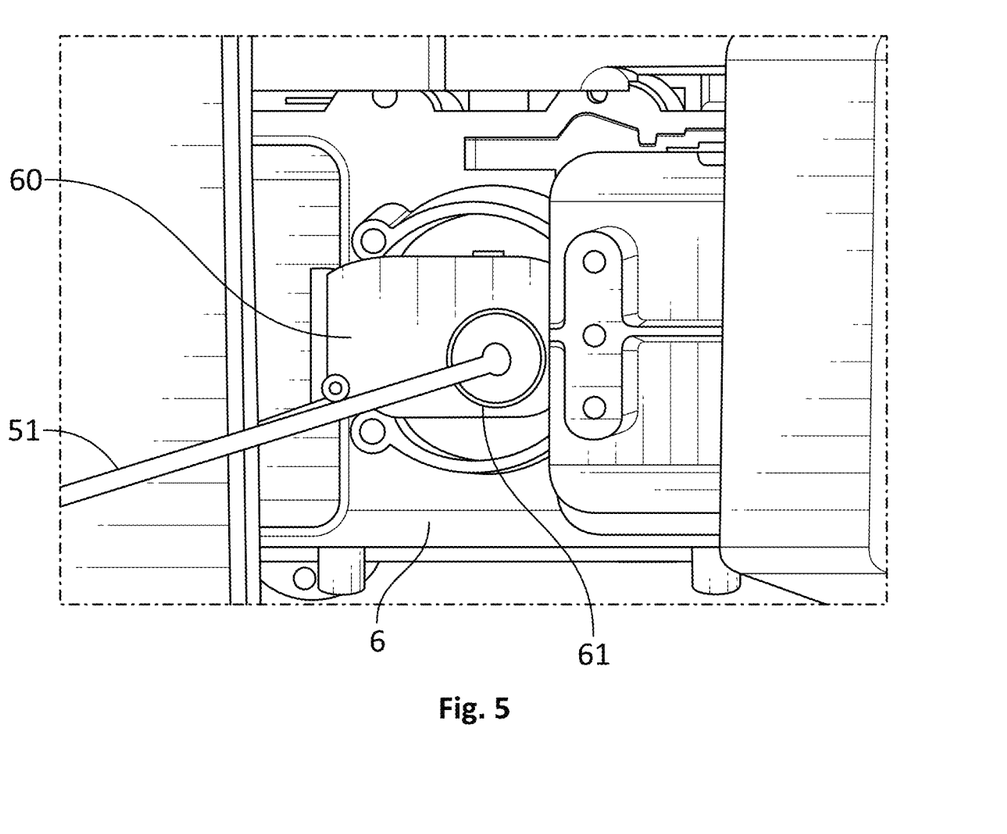
FIG. 5 is a diagram that shows a visual indication (e.g., a laser beam) of an exemplary sight embodiment in correct relationship with a system x-ray source that includes a target.

FIG. 5 is a diagram that shows a visual indication (e.g., a laser beam) of an exemplary sight embodiment attached to the cephalometric imaging module that is mounted in correct relationship with a system x-ray source that includes a target. As shown in FIG. 5, the laser beam 51 emitted by the attached sight 40 positioned between the two ear rods 13d and 13e strikes the target 61. Preferably, the target 61 is precisely positioned in front of the actual position of the x-ray source 6 as shown in FIG. 5. Alternatively, the target could have a precise offset or spaced 2D or 3D distance to the actual position of the x-ray source 6 and the sight 40 would then have a corresponding equal offset or spaced 2D or 3D distance to the two ear rods 13d and 13e of the second patient positioning and holding system 13.

The laser beam 61 emitted by the sight 40 held by the second patient positioning and holding system 13 materializes the axis passing through the two ear rods 13e and 13d. In one embodiment, the second patient positioning and holding system 13 can be configured so that an axis passing through the two ear rods 113d, 113e (e.g., the center) is orthogonal to the x-ray sensor 11 and aligned to the center line 100 of an x-ray beam of the x-ray source 6. When the laser beam 61 emitted by the sight 40 attached to the ear rods 13d and 13e strikes the filter 60 outside of the target 61, the cephalometric imaging module 10 must be adjusted by rotation about at least one of the two respective axis 20 and 30. When the laser beam 61 emitted by the sight 40 attached to the ear rods 13d and 13e strikes the filter 60 at the exact center of the target 61, the cephalometric module is correctly and properly positioned to the x-ray source 6 (e.g., coupled the column 4), with the center line 100 of the x-ray beam aligned with the ear rod axis (as shown in FIG. 2) and orthogonal to the sagittal plane 200 of the patient (when positioned on the holder 13) and to the cephalometric sensor 11.

Figure 6A:
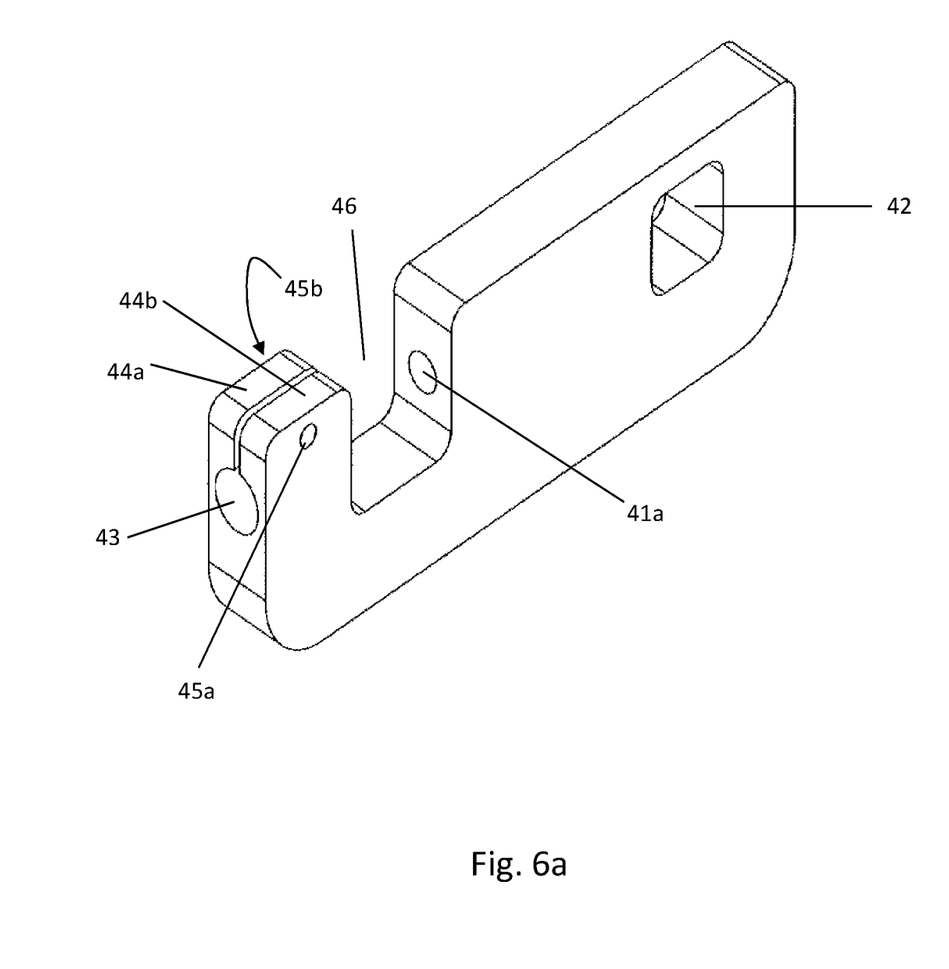
FIG. 6a is a diagram that shows a perspective view of an exemplary sight embodiment according to the application.
Figure 6B:
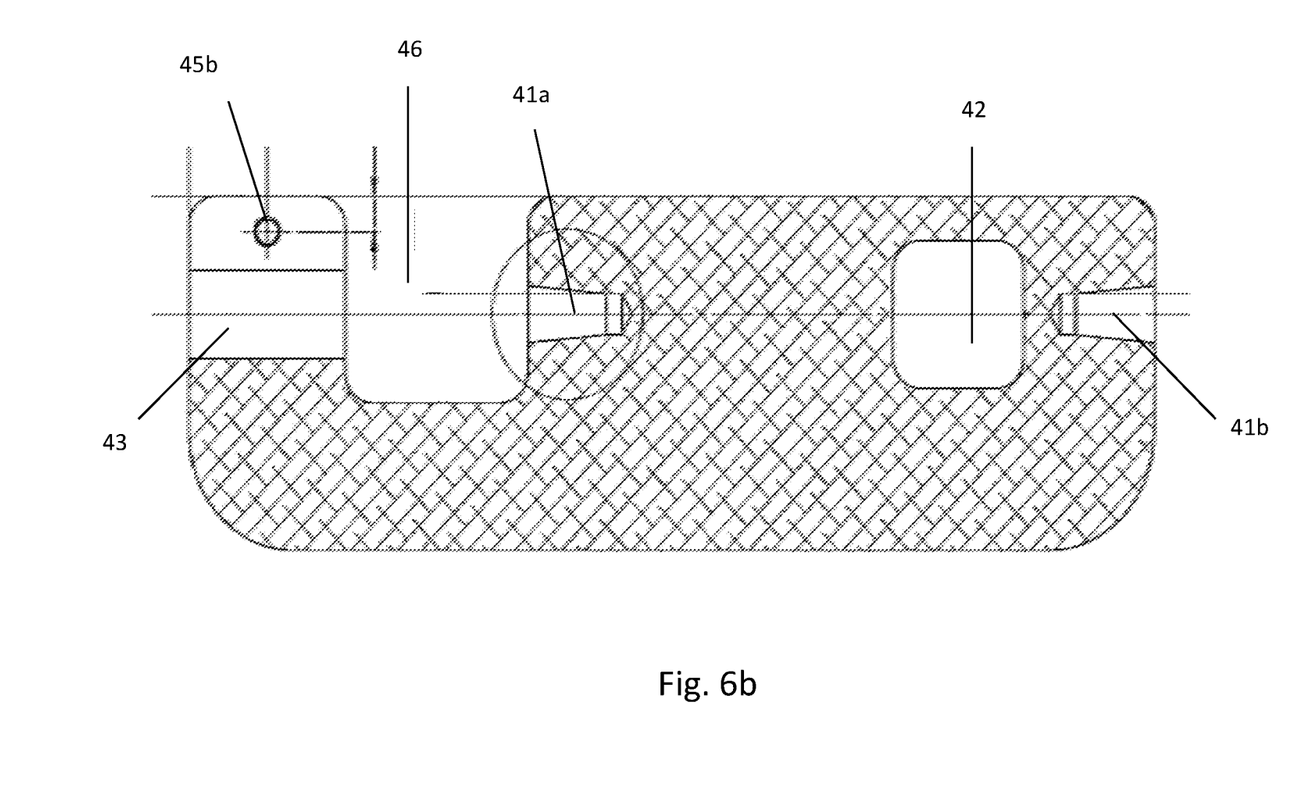
FIG. 6b is a diagram that shows a cross section of an exemplary sight embodiment according to the application along its longitudinal plane of symmetry according to the application.

FIGS. 6a-6b are diagrams that respectively show a perspective view and a longitudinal vertical cross section of an exemplary cephalometric alignment embodiment according to the application. As shown in FIGS. 6a-6b, the exemplary sight 40 can include a recess 46 to allow the passage of one ear rod holder (e.g., holder 13b) and two tapered bores 41a and 41b to receive and retain the two ear rods 13d and 13e. A bore 43 is designed for the insertion of the laser 50. For an easy installation of the laser 50 inside the bore 43, the front upper part of the sight 40 is divided into two flanges 44a and 44b separated by a small gap extending from the outer lateral surface of the flanges 44a and 44b to the bore 43. The flanges 44a and 44b and gap embodiment can increase the resilience of a part of the sight 40 that mounts the laser 50. By slightly increasing the gap between both flanges 44a and 44b, it is possible to increase the size of the bore 43 and to insert the laser 50 more easily inside the bore 43. Once the laser 50 is inserted, a fastener such as a screw (not represented) can be inserted into the holes 45a and 45b. Preferably at least one of the holes 45a and 45b is tapped. By turning the screw in the tapped hole, the gap between the two flanges 44a and 44b is narrowed (e.g., slightly or closed) and the laser 50 is tightly, securely and fixedly held inside the bore 43. Alternative ways to mount the laser 50 (e.g., detachably or integrally) to the sight 40 known to one of ordinary skill in the art can be used. In one embodiment, a hole 42 is provided in the lateral face of the sight 40. A ribbon or the like (not represented) can then be introduced through the hole 42 and can attach the sight 40 to the holding system 13, in order to prevent the sight 40 from falling from the holding system 13, that could damage the sight 40 or the laser 50 inserted into the sight 50.

As an alternative exemplary embodiment, the laser 50 can be replaced by a solid and rigid shaft inserted in the same way inside the bore 43 of the sight 50 and that can extend up to and reach the filter 60 supporting the target 61. In one embodiment, the laser 50 can be replaced by a telescoping rigid shaft inserted inside the bore 43 of the sight 50 and that can extend up to and reach the filter 60 supporting the target 61.

Once an adjustment is carried out so that the laser beam 51 of the sight 40 strike the center of the target 61, the technician can confirm, if desirable, the correctness of the cephalometric imaging module 10 adjustment by performing an exposure and reviewing an image of the patient holder 13 that also contains the radiopaque markers 16 and 17. One advantage of method embodiments using the sight 40 or cephalometric alignment devices according to the application is that a correct cephalometric imaging module 10 adjustment can be achieved quickly and easily, most probably at the first attempt. Thus, using embodiments of the sight 40 or cephalometric alignment devices according to the application can reduce or prevent performance of multiple back and forth operations of conventional adjustment and then verification by control images.

Figure 7:
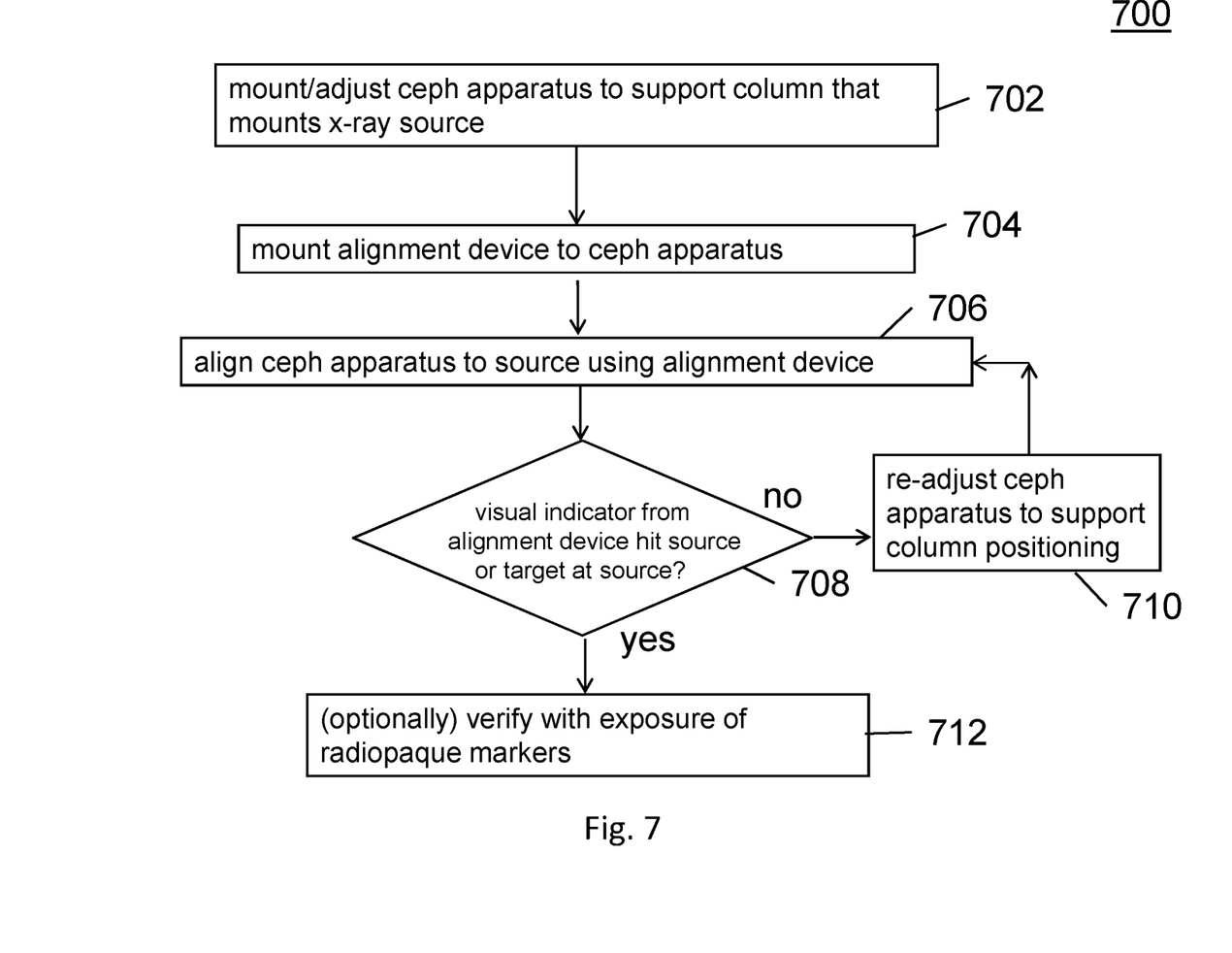
FIG. 7 is a flow chart that shows an exemplary method of installing and/or adjusting a cephalometric imaging apparatus at a dental extra-oral system according to embodiments of the application.

Referring to FIG. 7, a flow chart that shows an exemplary method of installing and/or adjusting a cephalometric imaging apparatus at a dental extra-oral system according to embodiments of the application will now be described. As shown in FIG. 7, the method installing a cephalometric imaging apparatus will be described with reference to and can be implemented by embodiments of radiographic dental extra-oral system shown in FIGS. 1a-1b; however, the method of FIG. 7 is not intended to be limited thereby.

As shown in FIG. 7, a cephalometric imaging apparatus can be mounted or attached to an adjustable support base of a dental extra-oral system (operation block 702). In one embodiment, the cephalometric imaging apparatus (e.g., the x-ray sensor collimator and/or a patient support) can be mounted at a cephalometric arm that is mounted to a vertical support mounting an x-ray source of a dental extra-oral system. Then, a cephalometric alignment device can be detachably mounted to the cephalometric imaging apparatus (operation block 704). As shown in FIG. 1a, the sight 40 is attached to both ear rods 13d, 13e (e.g., between). Alternatively, the cephalometric alignment device can be detachably attached to the cephalometric imaging module 10, the collimator 12, the sensor 11 or the like.

In order to obtain a skull profile image of the best quality, the sagittal plane of the skull must be parallel to the plane of the sensor at the time of the imaging and orthogonal to the median line of the x-ray beam. Consequently, when a cephalometric imaging apparatus is first installed in a dental site by a technician, it is necessary to adjust the position of the whole cephalometric imaging module relative to the x-ray source, prior to any cephalometric imaging of patients. As shown in FIG. 7, the indicator of the alignment device is used to align the whole cephalometric imaging apparatus relative to the x-ray source (operation block 706). For example, the whole cephalometric imaging apparatus can be moved for alignment adjustment (e.g., around at least one of both axis 20 and 30). In one embodiment, the visual indicator (e.g., beam 51) of the sight 40 is energized and compared by the technician to the x-ray source location. In one embodiment, the beam 51 can be compared to or aimed at a target on the x-ray source or coupled thereto (e.g., filter 60) by the technician. When the determination is that the visual indicator of the cephalometric alignment device is accurately aligned to the x-ray source, the installation process can be complete (operation block 708, yes). When the determination is that the visual indicator of the cephalometric alignment device is not accurately aligned to the x-ray source, control continues to a re-adjustment step where operations described in operation block 706 can be repeated, as needed (operation block 708, no). The result of operation block 708 (yes) is preferably that (i) the center line 100 of the x-ray beam is aligned with the sight 40 (e.g., and two ear canals of the patient positioned whenever subsequently imaged), (ii) the alignment ensures the sagittal plane of the patient will be orthogonal to the median line 100 of the x-ray beam, and (iii) the alignment ensures the plane of the cephalometric sensor will be orthogonal to the median line 100 of the x-ray beam. For example, Further, an optional process can be implemented where verification can be performed by an x-ray exposure of radiopaque markers attached to the cephalometric imaging apparatus (operation block 712). For example, a verification exposure of radiopaque markers (e.g., marker 18, 19) such as those shown in FIGS. 2a-2c can be installed on the holder 13 and performed.

Consistent with exemplary embodiments of the present application, a computer program utilizes stored instructions that perform on image data that is accessed from an electronic memory. As can be appreciated by those skilled in the image processing arts, a computer program for operating the imaging system in an exemplary embodiment of the present application can be utilized by a suitable, general-purpose computer system, such as a personal computer or workstation. However, many other types of computer systems can be used to execute the computer program of the present application, including an arrangement of networked processors, for example. The computer program for performing exemplary methods/apparatus of the present application may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing exemplary methods/apparatus of the present application may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present application may make use of various image manipulation algorithms and processes that are well known. It will be further understood that the computer program product embodiment of the present application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present application, are not specifically shown or described herein and may be selected from such algorithms, systems, hardware, components and elements known in the art.

In one embodiment, a method for operating an extra-oral imaging system can include providing a system base adjustable in at least one direction; mounting a cephalometric imaging sensor panel to the system base to provide a cephalometric imaging area formed with an x-ray source; providing a cephalometric patient positioning unit positioned between the x-ray source and the cephalometric imaging sensor panel so that x-rays impinge the cephalometric imaging sensor panel after radiating the cephalometric imaging area, the cephalometric patient positioning unit including at least one patient support having a controllable position relative to the cephalometric imaging sensor panel; and mounting an alignment sight to the least one patient support to provide a visual indication of alignment between the x-ray source and the at least one patient support. In one embodiment, cephalometric imaging can be performed on a part of the skull of the patient. In one embodiment, a method for servicing an extra-oral imaging system can include mounting an alignment sight to the least one patient support to provide a visual indication of alignment between the x-ray source and the at least one cephalometric patient support and aligning or servicing the same. In one exemplary embodiment, a visual indication of alignment can use a laser beam, a light beam, an optical pointer, or an extendable mechanical or electro-mechanical element, and/or a displayed rendition of a laser beam, a light beam, an optical pointer, or an extendable mechanical or electro-mechanical element, a electromagnetic beam, an ultraviolet beam, an ultrasonic beam or an infrared beam. In one embodiment, an alignment sight can include a display (mounted thereto) to display the x-ray source, the visual indication, or the visual indication and the x-ray source.

The invention has been described in detail, and may have been described with particular reference to a suitable or presently preferred embodiment, but it will be understood that variations and modifications can be effected within the spirit and scope of the invention. For example, exemplary alignment sight embodiments can be reciprocally moved between a retracted position and an alignment position in contrast to being detachable (e.g., after alignment and before scanning). Alternatively, exemplary alignment sight embodiments can be electronically detectable as transceivers mounted to alignment mechanisms (e.g., the x-ray source, and a collimator, ear rods or a part of a head support) that can be positioned by the technician (e.g., to determine a spatial relationship sufficient to show and/or instantiate alignment), then detected by remote sensors for real-time display to the technician on a display, a remote control with a display, a display included as part of the sight or the like). In one embodiment, such a display can show alignment and/or mis-alignment with indications of corrective movements or directional adjustments required of the technician to achieve alignment of the cephalometric device to the x-ray source. In one alternative embodiment, a visual indication of alignment (e.g., a sight can be mounted at the x-ray source) and a target (e.g., at a patient holder) can be reversed relative to the x-ray source and the patient holder/cephalometric device. In one embodiment, where a part of the cephalometric mount or a part of the cephalometric patient positioning unit can include at least one patient support having a controllable position indicative of an orthogonal axis to the cephalometric sensor and a medial location of an x-ray beam from the x-ray source. The presently disclosed exemplary embodiments are therefore considered in all respects to be illustrative and not restrictive. The scope of the invention is indicated by the appended claims, and all changes that come within the meaning and range of equivalents thereof are intended to be embraced therein.

Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims, and all changes that come within the meaning and range of equivalents thereof are intended to be embraced therein.

The invention claimed is:

1. An extra-oral imaging system, the extra-oral imaging system comprising:
    a base adjustable in at least one dimension;
    a cephalometric support mounted to the base and configured to position a cephalometric sensor about a cephalometric imaging area so that x-rays impinge the cephalometric sensor after radiating the cephalometric imaging area;
    a cephalometric patient positioning unit mounted to the cephalometric support, the cephalometric patient positioning unit positioned between an x-ray source and the cephalometric sensor, the cephalometric patient positioning unit comprising:
    at least one patient support having a controllable position relative to the cephalometric sensor or the x-ray source; and
    an alignment sight detachably mounted to the extra-oral imaging system to provide a visual indication of alignment between the x-ray source and the mounted alignment sight, where (i) the x-ray source comprises a target and the alignment sight is mounted to the at least one patient support or the cephalometric sensor to hold a remote projection unit pointed toward the target, or (ii) the at least one patient support or the cephalometric sensor comprises the target and the remote projection device is mounted at the x-ray source pointed toward the target.

2. The extra-oral imaging system of claim 1, where the alignment sight is configured to provide a real-time indication of alignment between the x-ray source and the mounted alignment sight.

3. The extra-oral imaging system of claim 1, where the x-ray source comprises a filter and the cephalometric sensor comprises a cephalometric imaging collimator.

4. The extra-oral imaging system of claim 1, where the x-ray source comprises a filter including the target, where the alignment sight is mounted to the least one patient support to hold the remote projection unit pointed toward the target.

5. The extra-oral imaging system of claim 1, where the visual indication of alignment is a laser beam, a light beam, an optical pointer, or an extendable mechanical or electromechanical element.

6. The extra-oral imaging system of claim 1, where the visual indication of alignment is a displayed rendition of an electromagnetic beam, an ultraviolet beam, an ultrasonic beam or an infrared beam.

7. The extra-oral imaging system of claim 1, where the at least one patient support is at least one temporal holding member.

8. The extra-oral imaging system of claim 1, where the alignment sight comprises a display to display the x-ray source, the visual indication, or the visual indication and the x-ray source.

9. The extra-oral imaging system of claim 1, where the cephalometric patient positioning unit is between a cephalometric imaging collimator and the cephalometric imaging sensor panel, where the cephalometric patient positioning unit comprises
    a forehead support;
    at least one temporal holding member, and
    a cephalometric Frankfort plane positioning indicator, where the at least one temporal holding member is adjustable in at least one direction, where the at least one direction is a distance between two temporal holders; and where the forehead support is adjustable in at least two dimensions or is adjustable in 3D spatial coordinates.

10. The extra-oral imaging system of claim 1, the extra-oral imaging system further comprising:
    a first mount mounted to the support base and configured to revolve the x-ray source and a first imaging sensor partially around a first imaging area; and
    a first patient positioning unit coupled to the first mount and positioned between the x-ray source and the first imaging sensor so that x-rays impinge the first imaging sensor after radiating the first imaging area, where the first patient positioning unit comprises:
    a patient positioning unit shield;
    a chin support coupled to the first patient positioning unit shield and includes a chin positioning element;
    a forehead support coupled to the first patient positioning unit shield; and
    a Frankfort plan positioning indicator.

11. The extra-oral imaging system of claim 1, where an x-ray filter is mounted near the x-ray source, the x-ray filter comprising a viewable alignment target, where the alignment sight is mounted to the least one patient support to hold a laser projection unit pointed toward the viewable alignment target.

12. A method for servicing a cephalometric imaging unit to an extra-oral imaging system, the method comprising:

mounting a cephalometric imaging unit to a system base, the system base adjustable in at least one direction and configured to support an x-ray source, the cephalometric imaging unit configured to mount a cephalometric sensor, the cephalometric imaging unit comprising the cephalometric sensor and a cephalometric patient positioning unit positioned between the x-ray source and the cephalometric sensor so that x-rays impinge the cephalometric sensor after radiating the cephalometric patient positioning unit;

mounting a cephalometric alignment device to the extra-oral imaging system; and aligning the cephalometric imaging unit in real-time using a visual indication of alignment to the x-ray source provided by the cephalometric alignment device, where (i) the x-ray source comprises a target and the cephalometric alignment device is mounted to the cephalometric imaging unit to hold a remote projection unit pointed toward the target, or (ii) the cephalometric imaging unit comprises the target and the remote projection device is mounted at the x-ray source.

13. The method of claim 12, where the cephalometric patient positioning unit comprises at least one patient support having a controllable position indicative of an orthogonal axis to the cephalometric sensor and a medial location of an x-ray beam from the x-ray source.

14. The method of claim 12, where the x-ray source comprises a filter and the cephalometric sensor comprises a cephalometric imaging collimator.

15. An extra-oral dental imaging system aligned by the method of claim 12.

16. The method of claim 12, where the cephalometric alignment device comprises a display to display the x-ray source, the visual indication, or the visual indication and the x-ray source.

17. The method of claim 16, where the visual indication of alignment is a displayed rendition of an electromagnetic beam, an ultraviolet beam, an ultrasonic beam or an infrared beam.

18. The method of claim 12, where the visual indication of alignment is a displayed rendition of an electromagnetic beam, an ultraviolet beam, an ultrasonic beam or an infrared beam.

19. An extra-oral imaging system, the extra-oral imaging system comprising:

a base adjustable in at least one dimension;

a cephalometric support mounted to the base and configured to position a cephalometric sensor about a cephalometric imaging area so that x-rays impinge the cephalometric sensor after radiating the cephalometric imaging area;

a cephalometric patient positioning unit mounted to the cephalometric support, the cephalometric patient positioning unit positioned between an x-ray source and the cephalometric sensor, the cephalometric patient positioning unit comprising:

at least one patient support having a controllable position relative to the cephalometric sensor or the x-ray source; and an alignment sight detachably mounted to the at least one patient support or the cephalometric sensor to provide a visual indication of alignment between the x-ray source and the mounted alignment sight, where the visual indication of alignment is a displayed rendition of an electromagnetic beam, an ultraviolet beam, an ultrasonic beam or an infrared beam.

20. An extra-oral imaging system, the extra-oral imaging system comprising:

a base adjustable in at least one dimension;

a cephalometric support mounted to the base and configured to position a cephalometric sensor about a cephalometric imaging area so that x-rays impinge the cephalometric sensor after radiating the cephalometric imaging area;

a cephalometric patient positioning unit mounted to the cephalometric support, the cephalometric patient positioning unit positioned between an x-ray source and the cephalometric sensor, the cephalometric patient positioning unit comprising:

at least one patient support having a controllable position relative to the cephalometric sensor or the x-ray source; and an alignment sight detachably mounted to the at least one patient support or the cephalometric sensor to provide a visual indication of alignment between the x-ray source and the mounted alignment sight, where the alignment sight comprises a display to display the x-ray source, the visual indication, or the visual indication and the x-ray source.

* * * * *